(12) United States Patent
Wu et al.

(10) Patent No.: US 10,319,092 B2
(45) Date of Patent: Jun. 11, 2019

(54) LOCALITY-BASED DETECTION OF TRAY SLOT TYPES AND TUBE TYPES IN A VISION SYSTEM

(71) Applicant: Siemens Healthcare Diagnostics Inc., Tarrytown, NY (US)

(72) Inventors: Wen Wu, Kirkland, WA (US); Benjamin Pollack, Jersey City, NJ (US); Yao-Jen Chang, Princeton, NJ (US); Guillaume Dumont, Paris (FR); Terrence Chen, Princeton, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 74 days.

(21) Appl. No.: 15/551,571

(22) PCT Filed: Feb. 16, 2016

(86) PCT No.: PCT/US2016/018112
§ 371 (c)(1),
(2) Date: Aug. 16, 2017

(87) PCT Pub. No.: WO2016/133926
PCT Pub. Date: Aug. 25, 2016

(65) Prior Publication Data
US 2018/0033140 A1 Feb. 1, 2018

Related U.S. Application Data

(60) Provisional application No. 62/117,916, filed on Feb. 18, 2015.

(51) Int. Cl.
*G06T 7/00* (2017.01)
*G01N 35/00* (2006.01)
(Continued)

(52) U.S. Cl.
CPC ..... *G06T 7/0012* (2013.01); *G01N 35/00732* (2013.01); *G01N 35/00871* (2013.01);
(Continued)

(58) Field of Classification Search
CPC ..... G01N 35/00732; G01N 2035/0498; G01N 2035/0091; G01N 2035/00881;
(Continued)

(56) References Cited

U.S. PATENT DOCUMENTS

2009/0285473 A1  11/2009  Li et al.
2011/0188743 A1   8/2011  Urushiya
(Continued)

FOREIGN PATENT DOCUMENTS

WO  2002/059828 A2  8/2002
WO  2014/152329 A1  9/2014
(Continued)

OTHER PUBLICATIONS

Extended EP Search Report dated Feb. 22, 2018 of corresponding European Application No. 16752922.1, 4 Pages.
(Continued)

*Primary Examiner* — Gregory F Cunningham

(57) ABSTRACT

A method for detecting properties of sample tubes is provided that includes extracting image patches substantially centered on a tube slot of a tray or a tube top in a slot. For each image patch, the method may include assigning a first location group defining whether the image patch is an image center, a corner of an image or a middle edge of an image, selecting a trained classifier based on the first location group and determining whether each tube slot contains a tube. The method may also include assigning a second location group defining whether the image patch is from an image center, a left corner of the image, a right corner of the image, a left middle of the image; a center middle of the image or a right
(Continued)

middle of the image, selecting a trained classifier based on the second location group and determining a tube property.

21 Claims, 12 Drawing Sheets

(51) Int. Cl.
| | | |
|---|---|---|
| *G06T 7/12* | (2017.01) | |
| *G06T 7/73* | (2017.01) | |
| *G06K 9/46* | (2006.01) | |
| *G06K 9/62* | (2006.01) | |
| *H04N 5/225* | (2006.01) | |
| *H04N 5/247* | (2006.01) | |
| *G01N 35/04* | (2006.01) | |

(52) U.S. Cl.
CPC ......... *G06K 9/4604* (2013.01); *G06K 9/6227* (2013.01); *G06K 9/6261* (2013.01); *G06K 9/6267* (2013.01); *G06T 7/0008* (2013.01); *G06T 7/12* (2017.01); *G06T 7/74* (2017.01); *G01N 2035/0091* (2013.01); *G01N 2035/00881* (2013.01); *G01N 2035/0498* (2013.01); *G06T 2207/30108* (2013.01); *H04N 5/2256* (2013.01); *H04N 5/247* (2013.01)

(58) Field of Classification Search
CPC ............ G01N 35/00871; G06T 7/0008; G06T 2207/30108; G06T 7/12; G06T 7/74; G06T 7/0012; G06K 9/6267; G06K 9/6261; G06K 9/6227; G06K 9/4604; H04N 5/247; H04N 5/2256
USPC ......................................................... 382/128
See application file for complete search history.

(56) References Cited

U.S. PATENT DOCUMENTS

2014/0063241 A1    3/2014   Li et al.
2014/0305227 A1   10/2014   Johns

FOREIGN PATENT DOCUMENTS

| WO | WO-2014152329 A1 * | 9/2014 | ............ G01N 21/253 |
| WO | 2015/191702 A1 | 12/2015 | |
| WO | WO-2015191702 A1 * | 12/2015 | ............ G01N 21/952 |
| WO | WO-2016133926 A1 * | 8/2016 | ....... G01N 35/00732 |

OTHER PUBLICATIONS

PCT International Search Report and Written Opinion dated May 2, 2016 (9 Pages).

* cited by examiner

LOCALITY-BASED DETECTION OF TRAY SLOT TYPES AND TUBE TYPES IN A VISION SYSTEM

RELATED APPLICATION

This application claims priority to U.S. Provisional Application Ser. No. 62/117,916 entitled "LOCALITY-BASED DETECTION OF TRAY SLOT TYPES AND TUBE TYPES IN A VISION SYSTEM" filed on Feb. 18, 2015, the disclosure of which is hereby incorporated by reference in its entirety herein.

TECHNOLOGY FIELD

The embodiments disclosed herein relate in general to characterizing tray slots and tubes in a tray of an automated vision system and, more particularly, to capturing images of a tube tray to determine characteristics of the tray slots and tubes held within the tray.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) into which tubes or vials containing patient samples have been loaded. Because of the variety of assays needed in a modern IVD lab, and the volume of testing necessary to operate a lab, multiple analyzers are often employed in a single lab. Between and amongst analyzers, automation systems may also be used. Samples may be transported from a doctor's office to a lab, stored in the lab, placed into an automation system or analyzer, and stored for subsequent testing.

Storage and transport between analyzers is typically done using trays. A tray is typically an array of several patient samples stored in test tubes. These trays are often stackable and facilitate easy carrying of multiple samples from one part of the laboratory to another. For example, a laboratory may receive a tray of patient samples for testing from a hospital or clinic. That tray of patient samples can be stored in refrigerators in the laboratory. Trays of patient samples can also be stored in drawers. In some automation systems, an analyzer can accept a tray of patient samples and handle the samples accordingly, while some analyzers may require that samples be removed from trays by the operator and placed into carriers (such as pucks) before further handling. Trays are generally passive devices that allow samples to be carried and, in some cases, arranged in an ordered relationship.

Generally, information about sample tubes stored in a tray is not known until an operator or sample handling mechanism interacts with each tube. For example, a sample handling robot arm may pick up a tube, remove it from the tray, and place it into a carrier. The carrier can then travel to a decapper station to remove any possible cap and pass by a barcode reader so that a barcode on the side of the tube can be read to reveal the contents of the tube. In many prior art sample handling mechanisms, the identity of the tube is not known until after the tube is removed from the tray. In this manner, all tubes in a tray will often be handled the same way until after a tube is placed onto a carrier in an automation system.

SUMMARY

Embodiments provide a method for detecting properties of sample tubes. The method includes receiving a series of images of a tray acquired by one or more cameras. The tray includes a plurality of tube slots. The method also includes extracting, using a processor, a plurality of image patches from each image, wherein each of the plurality of image patches are substantially centered on one of a tube slot and a tube top. The method also includes assigning, to each image patch, a first location group that defines whether the image patch is from one of: a center of the image, a corner of the image, and a middle edge of the image and selecting, for each image patch, based on the first location group, a trained classifier to use in processing the image patch. The method further includes automatically determining, using the processor, from the plurality image patches, whether each tube slot in the tray contains a tube using the trained classifier for each image patch.

According to an embodiment, the tray is configured to fit within a portion of a drawer movable between an open position and a closed position and the series of images of the tray are acquired via the one or more cameras as the drawer is moved between the open and the closed position.

According to another embodiment, the method further includes assigning, to each image patch, a second location group that defines whether the image patch is from one of: the center of the image, a left corner of the image, a right corner of the image, a left middle of the image; a center middle of the image and a right middle of the image. The method further includes selecting, for each image patch, based on the second location group, the trained classifier to use in processing the image patch. When it is determined that one or more of the tube slots contains a tube, the method further includes automatically determining, using the processor, from the plurality image patches, at least one property of each of the tubes contained in the one or more tube slots.

In yet another embodiment, determining at least one property of each of the tubes further comprises automatically determining, using the processor, from the plurality image patches, whether each of the tubes contained in the one or more tube slots has a cap based on the corresponding trained classifier.

According to an aspect of an embodiment, determining at least one property of each of the tubes further comprises automatically determining, using the processor, from the plurality image patches, whether each tube contained in the one or more tube slots has a tube-top sample cup or is a plain tube based on the corresponding trained classifier.

According to another aspect of an embodiment, receiving the series of images further includes receiving the series of images from a first camera and a second camera adjacent to the first camera and extracting the plurality of image patches further includes extracting image patches from each image received from the first camera and extracting image patches from each image received from the second camera. Assigning the second location group further includes assigning the second location group to each image patch extracted from images received from the first camera horizontally symmetric to each image patch extracted from images received from the second camera and selecting the trained classifier further includes selecting the same trained classifier for each image patch extracted from images received from the first camera that is horizontally symmetric to each image patch extracted from images received from the second camera.

In one embodiment, the left corner of the image, the right corner of the image, and the center middle of the image each comprise a plurality of image patches and assigning the second location group horizontally symmetrical further comprises includes using a row of image patches from of one of the first camera and the second camera as a reference location and aligning image patches from the other of the first camera and the second camera to the reference location.

In another embodiment, each image includes a matrix of three rows of tube slots and three columns of tube slots and the plurality of image patches comprise a matrix of three rows of image patches and three columns of image patches. Each image patch corresponds to a location of one of the tube slots in the image.

Embodiments provide a method for offline image patch classifier training. The method includes receiving a series of images of a tray having a plurality of tube slots from a plurality of cameras and extracting a plurality of image patches from each image. Each of the plurality of image patches are substantially centered on one of a tube slot and a tube top. The method also includes providing, using a processor, each image patch of the plurality of images to a classifier and collecting, using the processor, image patch data for each image patch provided to the classifier, the data indicating one of: whether each tube slot in the tray contains a tube; whether each of the tubes contained in the one or more tube slots has a cap; and whether each tube contained in the one or more tube slots has a tube-top sample cup or is a plain tube. The method also includes determining, using the processor, image patch classifiers corresponding to each image patch based on the image patch data.

According to an embodiment, extracting the plurality of image patches from each image further includes extracting, over time, multiple image patches substantially centered on one of the same tube slot and the same tube top.

According to another embodiment, the classifier is a random forest classifier, a support vector machine classifier, or a probabilistic boosting tree classifier.

Embodiments provide a vision system for use in an in vitro diagnostics environment that includes a tray comprising a plurality of slots arranged in a matrix of rows and columns. Each tube slot is configured to receive a sample tube. The system also includes a surface configured to receive the tray and an image capture system having a first camera configured to capture a series of images of the tray. The system further includes a processor configured receive the series of images of the tray captured by the first camera and extract a plurality of image patches from each image of the series of images. Each of the plurality of image patches are substantially centered on one of the plurality of tube slots or a tube top. The processor is also configured to assign, to each image patch, a first location group that defines whether the image patch is from one of: the center of the image, a corner of the image, and a middle edge of the image and select, for each image patch, based on the first location group, a trained classifier to use in processing the image patch. The processor is further configured to automatically determine, from the plurality of image patches, whether each tube slot in the tray contains a corresponding sample tube using the trained classifier for each image patch.

According to an embodiment, the image capture system further includes a second camera adjacent to the first camera and configured to capture images of the tray proximate to the images captured by the first camera.

According to another embodiment, the surface comprises a portion of a drawer movable between an open and a closed position and the image of the tray is captured via the first camera and the second camera as the drawer is moved between the open position and the closed position.

In yet another embodiment, the processor is further configured to extract image patches from each image received from the first camera and extract image patches from each image received from the second camera and assign the second location group to each image patch extracted from images received from the first camera horizontally symmetric to each image patch extracted from images received from the second camera. The processor is further configured to select the same trained classifier for each image patch extracted from images received from the first camera that is horizontally symmetric to each image patch extracted from images received from the second camera.

In an aspect of an embodiment, the left corner of the image, the right corner of the image, and the center middle of the image to each include a plurality of image patches and the processor is further configured to assign the second location group to each image patch extracted from images received from the first camera horizontally symmetric to each image patch extracted from images received from the second camera by using a row of image patches from of one of the first camera and the second camera as a reference location and aligning image patches from the other of the first camera and the second camera to the reference location.

In another aspect of an embodiment, the image capture system further includes a light emitting diode (LED) board that includes a first hole configured to facilitate the capturing of the series of images of the tray from the first camera, a second hole configured to facilitate the capturing of the series of images of the tray from the second camera and a plurality of LEDs arranged in a circular manner around each of the first hole and the second hole and configured to provide light on the tray.

In one embodiment, the processor is further configured to assign, to each image patch, a second location group that defines whether the image patch is from one of: the center of the image, a left corner of the image, a right corner of the image, a left middle of the image; a center middle of the image and a right middle of the image. The processor is further configured to select, for each image patch, based on the second location group, the trained classifier to use in processing the image patch. When it is determined that one or more of the tube slots contains a tube, the processor is further configured to automatically determine from the plurality image patches, at least one property of each of the tubes contained in the one or more tube slots.

In another embodiment, the processor is further configured to automatically determine, from the plurality image patches, whether each of the tubes contained in the one or more tube slots has a cap based on the corresponding trained classifier.

According to one embodiment, the processor is further configured to automatically determine, from the plurality image patches, whether each tube contained in the one or more tube slots has a tube-top sample cup or is a plain tube based on the corresponding trained classifier.

According to one embodiment, each image includes a matrix of three rows of tube slots and three columns of tube slots and the plurality of image patches include a matrix of three rows of image patches and three columns of image patches, each image patch corresponding to a location of one of the tube slots in the image.

Additional features and advantages of this disclosure will be made apparent from the following detailed description of illustrative embodiments that proceeds with reference to the accompanying drawings.

BRIEF DESCRIPTION OF THE DRAWINGS

The foregoing and other aspects of the embodiments disclosed herein are best understood from the following detailed description when read in connection with the accompanying drawings. For the purpose of illustrating the embodiments disclosed herein, there is shown in the drawings embodiments that are presently preferred, it being understood, however, that the embodiments disclosed herein are not limited to the specific instrumentalities disclosed. Included in the drawings are the following Figures.

DESCRIPTION OF EXEMPLARY EMBODIMENTS

This application relates to several of the concepts described in PCT Application No.: PCT/US14/27217, and U.S. Application No. 62/010,370 to Wu et al., which are incorporated, herein by reference.

It is desirable to ascertain various pieces of information relating to a tray and the tubes. It is desirable to obtain this information and other pieces of information quickly, without expensive equipment, and without handling or touching the tubes. Such knowledge allows for an efficient and streamlined processing of the tubes, as well as for reduced setup and maintenance costs. This information is valuable in an IVD environment in which a sample handler is processing the tubes and moving the tubes to analyzers for testing and analysis. Embodiments of the present invention are particularly well suited for, but in no way limited to, IVD environments.

Embodiments include systems and methods of training classifiers for image patches extracted from captured images of tubes held within a tube tray and using the trained classifiers for each patch to determine whether slots are empty or include tubes and whether the tubes have a cap or tube-top sample cup. In some embodiments, image patches are grouped by location based on light distribution. In other embodiments, image patches are grouped by location based on camera view perspective. The trained classifiers are selected based on their grouping to use in determining slot type and tubes types.

In some embodiments, an automated vision system may be used to acquire images of the tube trays and tubes held within the tube trays. Some embodiments include capturing images of trays that are manually placed and aligned in an automation system. For example, automation systems may provide a flat surface with guide rails and allow the operator to manually align keying features on the trays to the rails and push the trays to the working area.

Some embodiments may include an automated drawer vision system (DVS) comprising a drawer for loading and unloading tube trays on which sample tubes are contained. The images of the trays may be acquired via one or more cameras, mounted above an entrance area of the drawer, as the drawer is moved between an open position and a closed position (e.g., working area position). The images may be used to characterize the tray as well as the tubes held on the tray. In particular, according to embodiments, by analyzing the images, various features may be determined, such as whether slots are empty or include tubes and whether the tubes have a cap or tube-top sample cup.

Figure 1A:
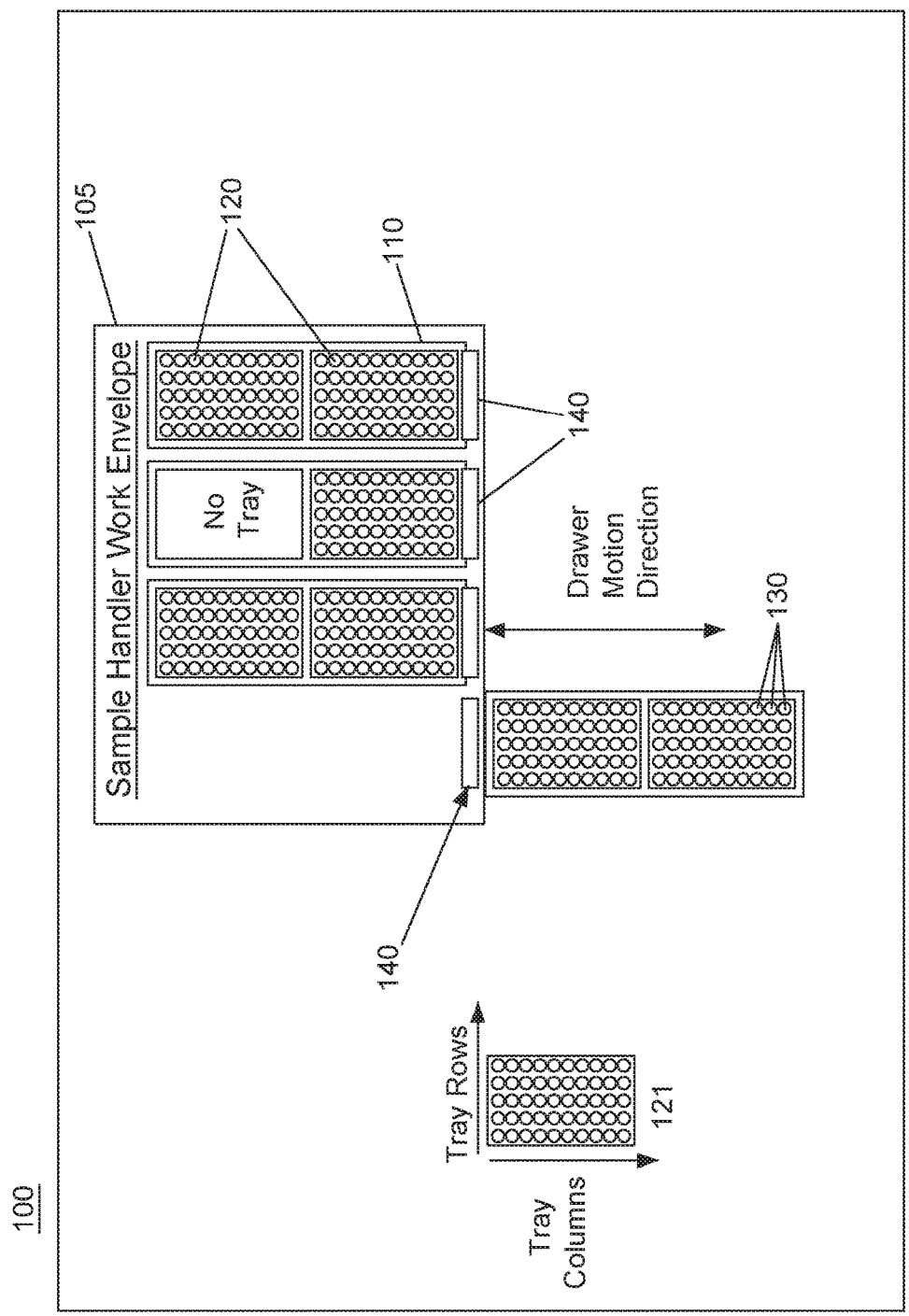
FIG. 1A is a representation of a system for characterizing through image analysis tube trays and tubes held in a drawer, according to an embodiment.

FIG. 1A is a representation of an exemplary drawer vision system 100 in which tube trays 120 and tubes 130 contained thereon are characterized by obtaining and analyzing images thereof, according to an embodiment. One or more drawers 110 are movable between an open and a closed position and are provided in a work envelope 105 for a sample handler. One or more tube trays 120 may be loaded into a drawer 110 or may be a permanent feature of the drawer 110. Each tube tray 120 has an array of rows and columns of slots (as depicted in exemplary tray 121) in which tubes 130 may be held.

According to embodiments, images are taken of a tube tray 120. The images are analyzed to determine characteristics of the tube tray 120 and the tubes 130. A moving-tray/fixed camera approach is used, according to embodiments provided herein, to capture the images for analysis thereof. As the tube tray 120 is moved into the work envelope 105 by, for example, manually or automatically pushing in the drawer 110, an image capture system 140 is used to take images of the tube tray 120 and the tubes 130 contained thereon.

The image capture system 140 may include one or more cameras positioned at or near the entrance to the work envelope 105. The one or more cameras may be positioned above the surface of the tube tray 120. For example, the cameras may be placed fifty to seventy inches above the surface to capture a high resolution image of the tube tray 120. Other distances and/or positioning may also be used depending on the features of the cameras and the desired perspective and image quality. Optionally, the image capture system 140 may include one or more lighting sources, such as an LED flash.

Figure 1B:
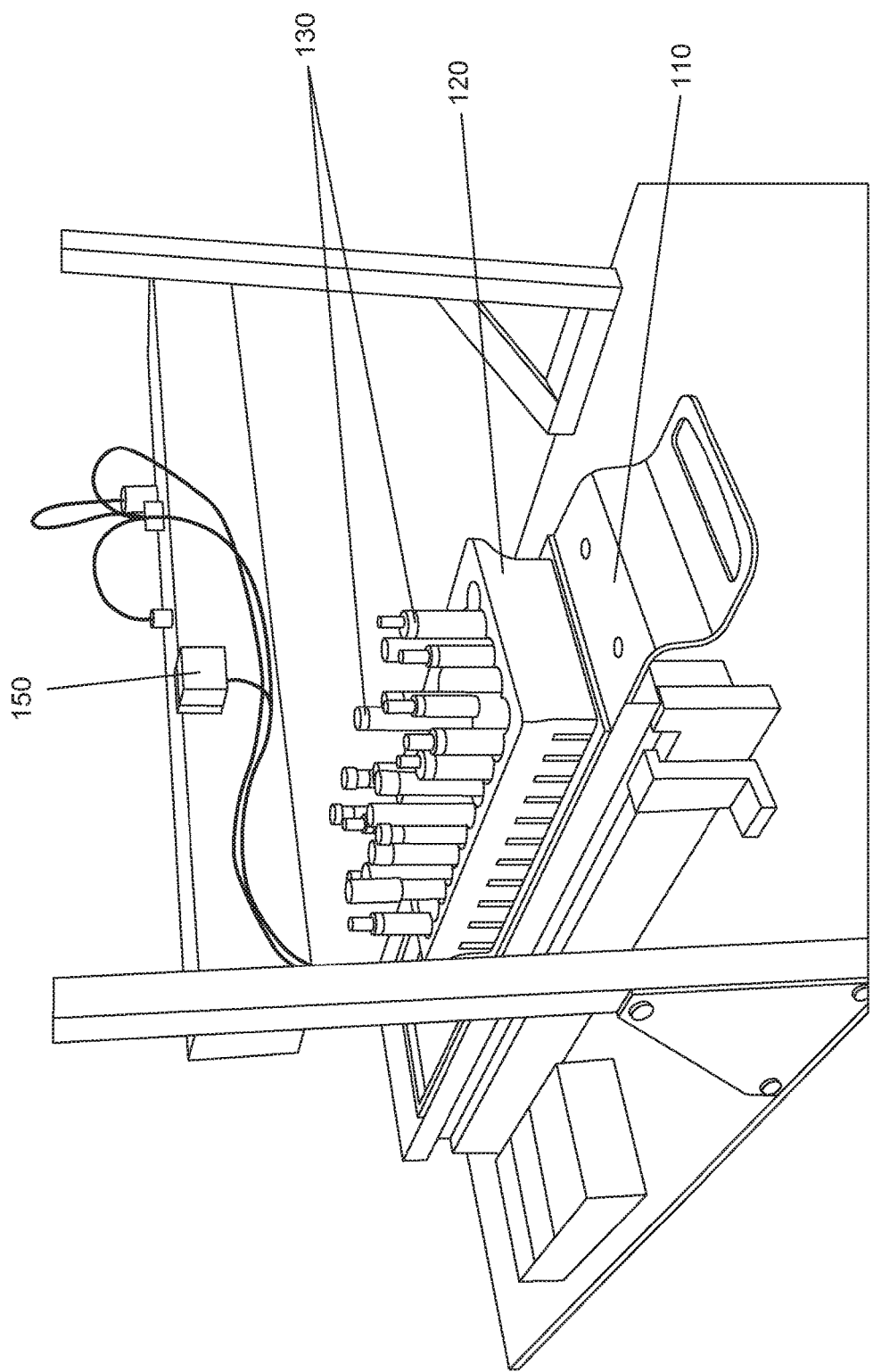
FIG. 1B shows an exemplary drawer vision system test harness including an image capture system which may be used for offline classifier training, according to embodiments disclosed herein.

FIG. 1B shows an exemplary test harness of an exemplary drawer vision system that may be used with embodiments disclosed herein. As shown in FIG. 1B, may include an LED board 150, having cameras (not shown) disposed therein, is positioned above the surface of the tube tray 120 holding tubes 130 and disposed on drawer 110. The drawer 110 shown in the embodiment at FIG. 1B is configured to hold two 55-slot trays or six 15-slot trays. Embodiments may, however, include trays configured to hold trays having different numbers of slots and having different sizes.

Figure 1C:
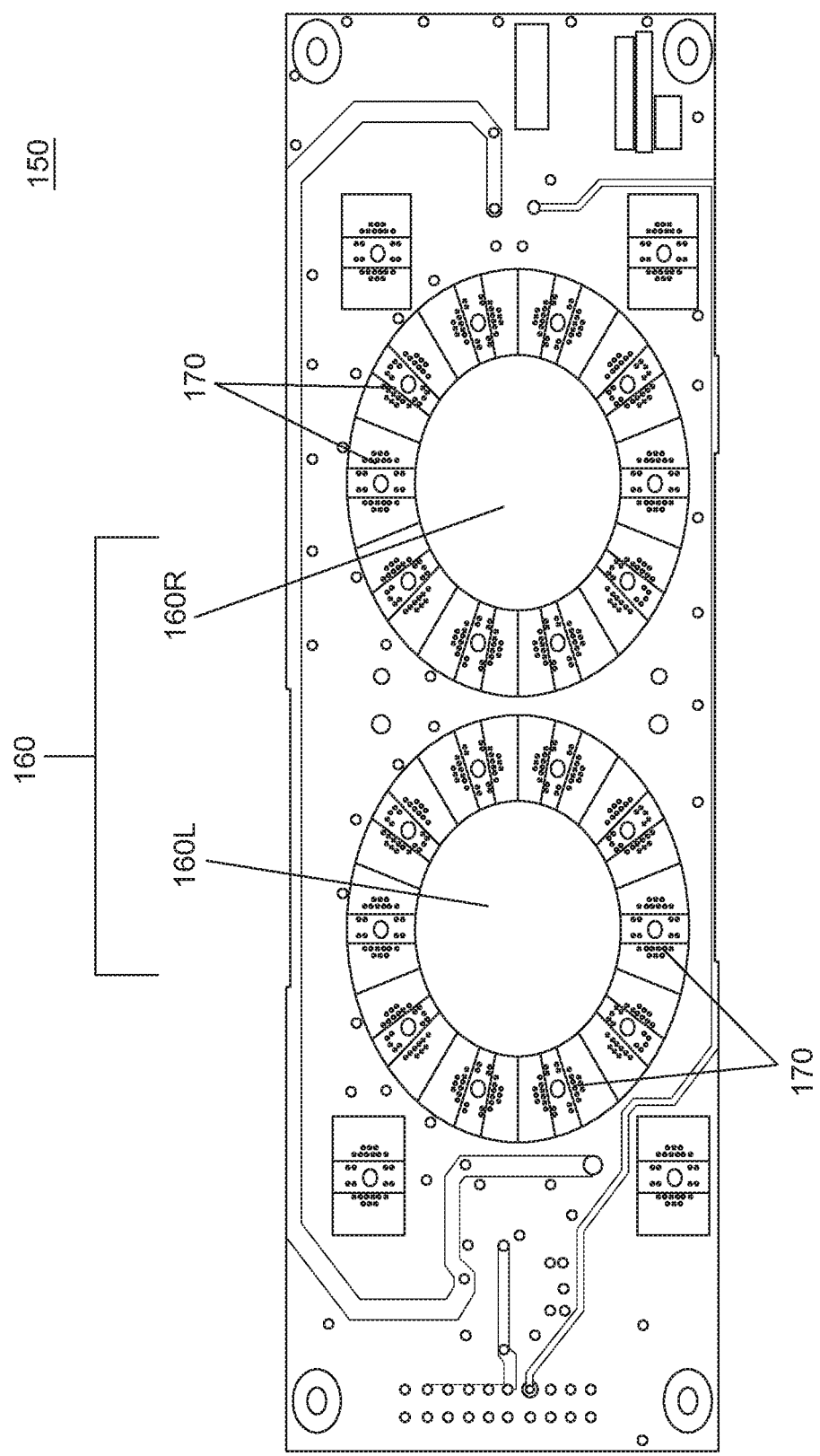
FIG. 1C shows an exemplary LED board having a plurality of LEDs arranged in a circular manner around a left hole and a right hole, that may be used with embodiments.

In the embodiments described herein, two cameras, a left camera and a right camera are used. FIG. 1C shows an exemplary LED board 150 having holes 160 that include a left hole 160L and a right hole 160R. The LED board 150 also includes a plurality of LEDs 170 arranged in a circular manner to provide light on the tube trays 120 and tubes 130.

The image capture system 140 captures multiple perspectives of the row of the tubes 130 as the row is advanced into the work envelope 105 as described in PCT Application No.: PCT/US14/27217, which is incorporated herein by reference.

Figure 2:
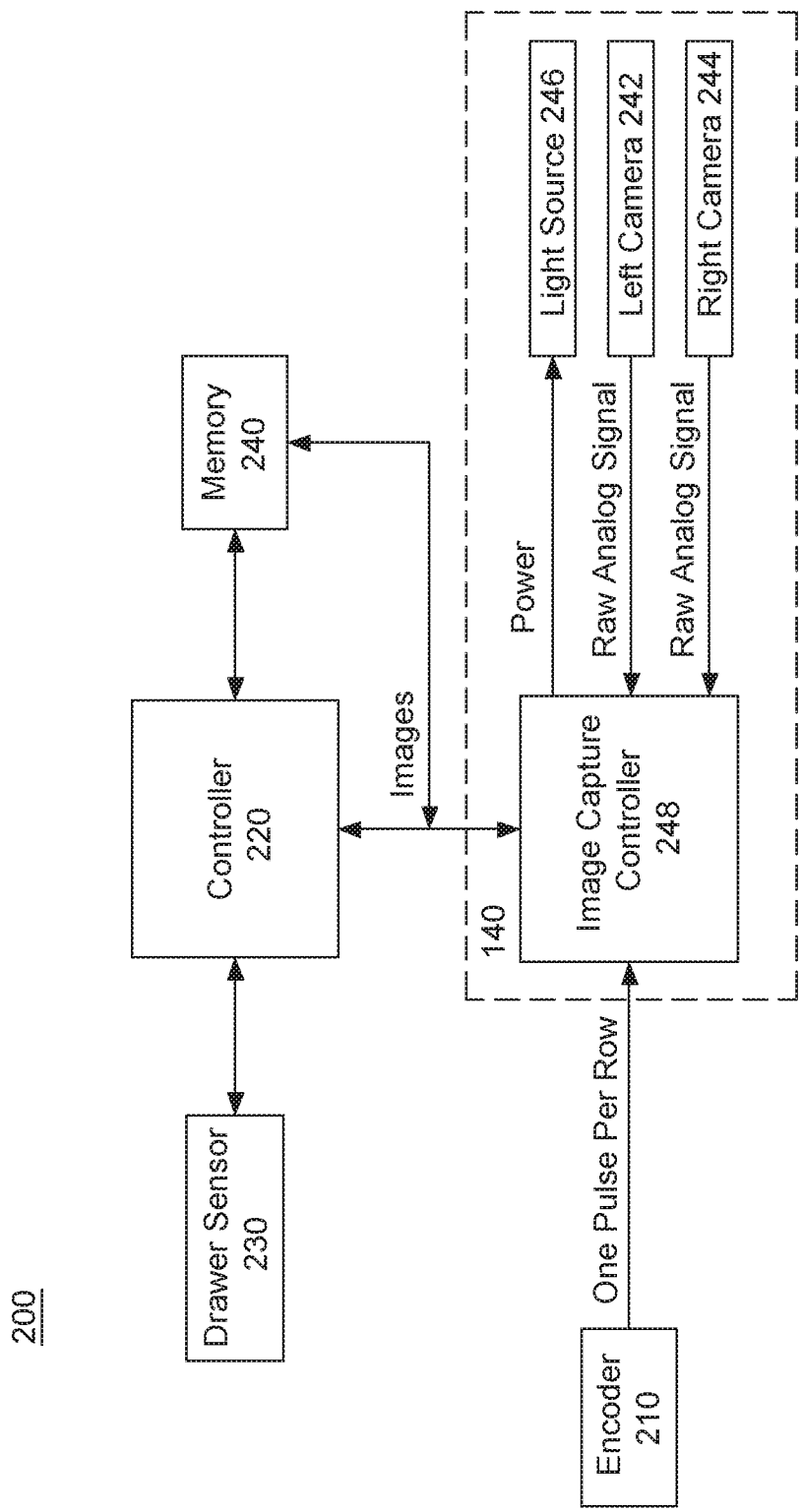
FIG. 2 shows a block diagram representation of a system for characterizing, through image analysis, the tube trays and the tubes contained thereon held in a drawer, according to an embodiment.

FIG. 2 shows a block diagram representation of a system 200 for characterizing, through image analysis, the tube trays 120 and the tubes 130 contained thereon held in a drawer 110, according to an embodiment. The image capture system 140, according to an embodiment, includes two cameras, a left camera 242 and a right camera 244. Additional or fewer cameras may be included depending on the size of the drawers 110 and the tube trays 120, as well as the desired image quality and image perspective. A light source 246 and an image capture controller 248 are also part of the image capture system 140.

An encoder 210, such as a quadrature encoder may be used to determine when a row of the tube tray 120 is moved into a centered or substantially centered position beneath the one or more cameras 242, 244. The encoder 210 transmits a signal (i.e., a pulse) to the image capture controller 248 upon detection of movement of the tube tray 120 corresponding to a new row of the tube tray 120 moving into a centered or substantially centered position beneath the one or more cameras 242, 244. The signal serves as an instruction for the image capture controller 248 to instruct the cameras 242, 244 to take an image upon receipt of the signal.

A controller 220 is provided for managing the image analysis of the images taken by the cameras 242, 244. Upon detection of the closing of the drawer 110, the image capture controller 248 provides the images to the controller 220 for downloading and processing. The controller 220 is, according to an embodiment, part of a sample handler that is used in the IVD environment to handle and move the tube trays 120 and the tubes 130 between storage locations, such as the work envelope 105, to analyzers. The image analysis performed by the controller 220 serves to instruct the sample handler on the various determined characteristics of the tube tray 120 and the tubes 130, thus allowing the sample handler to accordingly handle and process the tube tray 120 and the tubes 130.

The one or more memory devices 240 are associated with the controller 220. The one or more memory devices 240 may be internal or external to the controller 220.

One or more drawer sensors 230 may be connected to the controller 220 to indicate when the drawer 110 is fully closed and/or when the drawer 110 is fully opened. According to an embodiment, the drawer 110 being fully closed serves as an indication to begin image processing of the captured and stored images. When the drawer 110 is fully closed, the drawer sensor 230 sends a signal to the controller 220.

Figure 3:
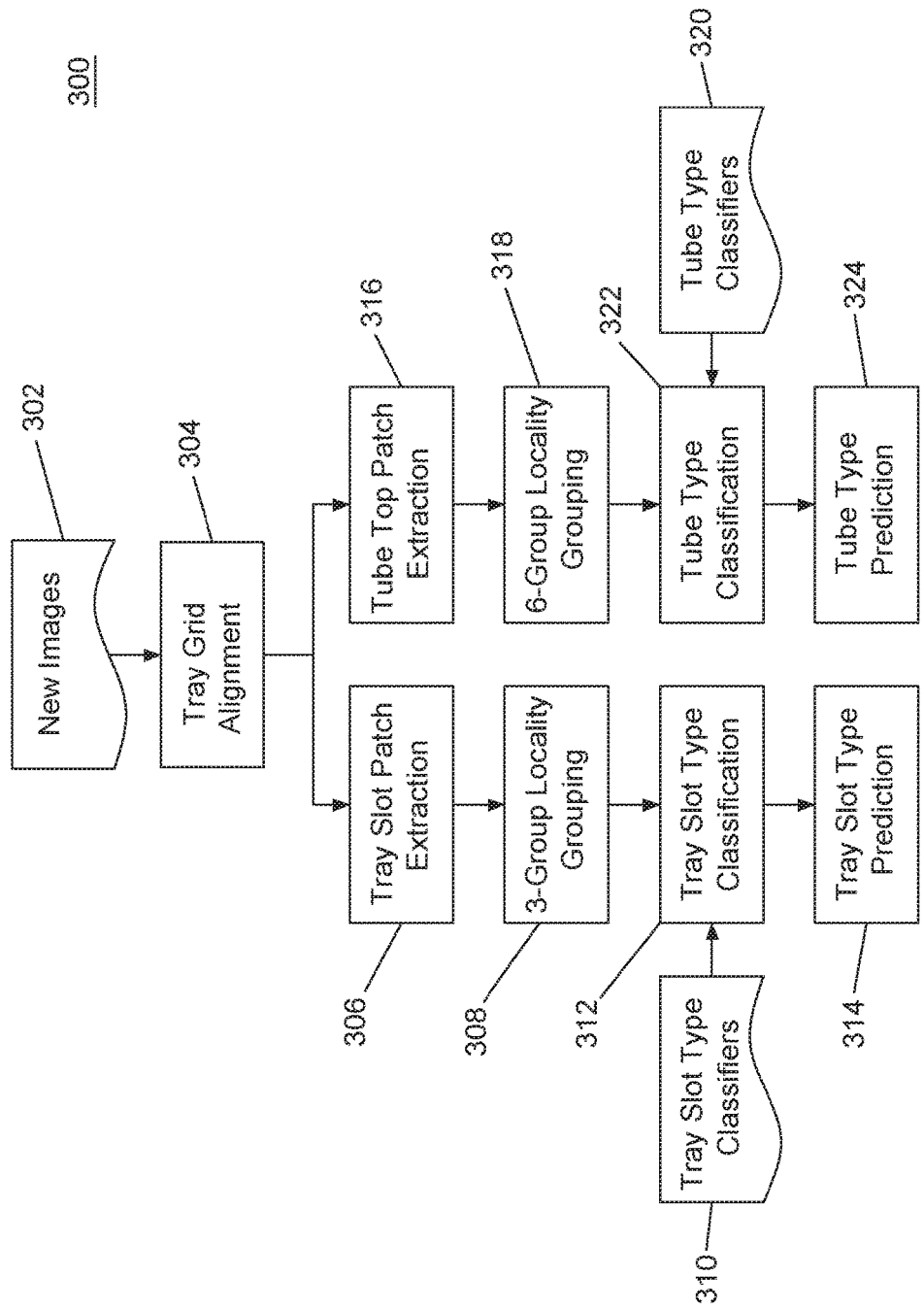
FIG. 3 is a flowchart illustrating a method of detecting properties of sample tubes according to embodiments described herein.
Figures 4A, 4B:
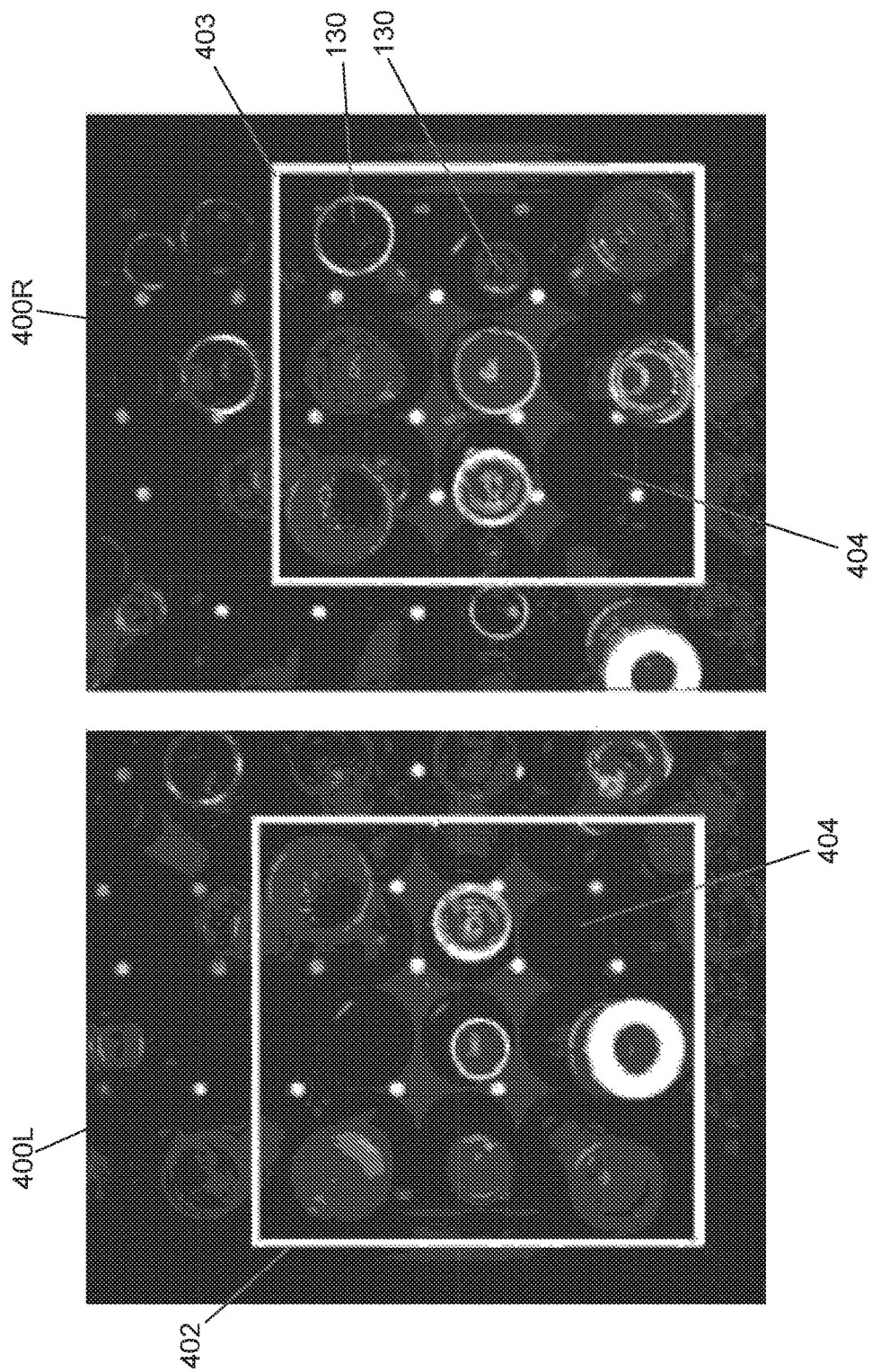
FIG. 4A is an image of an area of an exemplary tray captured by a left camera, according to an embodiment.
FIG. 4B is an image of an area of an exemplary tray captured by a right camera, according to an embodiment.

FIG. 3 is a flowchart illustrating a method 300 of determining tray slot types and sample tube types. As shown in FIG. 3, images are acquired at step 302. FIG. 4A is an image 400L of an area 402 of an exemplary tray captured by the left camera 242, according to an embodiment. FIG. 4B is an image of an area 403 of an exemplary tray 120 captured by the right camera 244, according to an embodiment. The image 400L includes a 3 row×3 column slot area 402 of the tray 120 including tubes 130. The image 400R includes a 3 row×3 column slot area 403 of the tray 120 including tubes 130.

The tray grid is aligned at 304. In some embodiments, the tray 120 may be aligned using fiducial markers disposed on the trays, as described in application entitled "Image-based Tray Alignment and Tube Slot Localization for Drawer Vision System" (Docket No. 2014P22904US). For example, the trays may be aligned using determined offsets between projected markers on the trays determined via offline calibration and detected markers on the trays during online operation.

After the tray grid is aligned at step 304, the method may include steps 306-314 to determine a tray slot type (e.g., whether slot is empty or not empty) and/or steps 316-324 to determine a tube type (e.g., plain tube, tube with a cap or tube with a tube-top sample cup).

The method of predicting the tray slot type is described first. At step 306, the tray slot patch may be extracted. That is, a plurality of image patches may be extracted over time from each image captured by cameras 242 and 244. Each image patch may be substantially centered on one of the tube slots 404 or a top of one of the tubes 130, shown in the images at FIG. 4A and FIG. 4B. In some embodiments, the tray slot patch may be extracted, as described in U.S. Patent Application Publication No. 2018/0045747 entitled "Image-based Tray Alignment and Tube Slot Localization in a Vision System.", by projecting tube slot grid points on the trays based on the offset obtained from the tray alignment and using the grid points to extract tube slots from the images.

Figure 5:
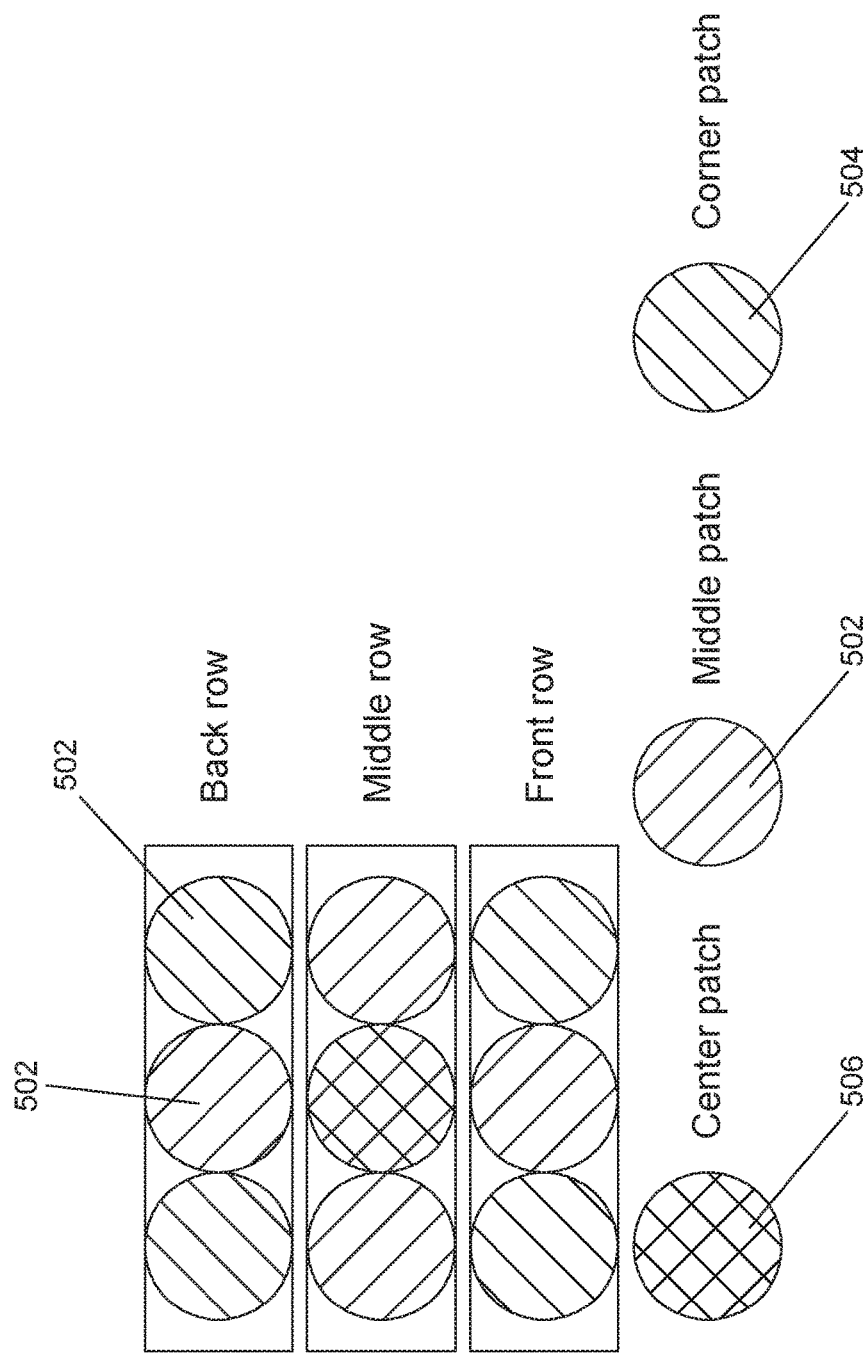
FIG. 5 is a diagram illustrating a plurality of image patches grouped into three image patch groups, according to an embodiment.

At step 308, a first location group may be assigned to each image patch. FIG. 5 is a diagram illustrating a plurality of image patches grouped into three image patch groups, according to an embodiment. As shown in FIG. 5, the first location group includes a middle patch group 502, a corner patch group 504 and a center patch 506. The first location group is based on the camera view perspective. The center patch 506 corresponds to one tube slot location, and the middle patch group and corner patch group each corresponds to four tube slot locations. The grouping applies to both the left camera 242 and the right camera 244.

Prior to selecting a trained classifier for each image patch based on the first location group at step 312 during online operation, image patch classifiers corresponding to each image patch are trained offline at step 310. An exemplary method for training image patch classifiers may include receiving a series of images of a tray having a plurality of tube slots from a plurality of cameras, such as cameras 242 and 244. Image patches may be extracted from each image and fed or provided to a classifier or algorithm. Embodiments may include using different types of classifiers, such as for example, a random forest classifier, a support vector machine classifier, and a probabilistic boosting tree classifier.

Image patch data may be collected, using a processor, for each image patch provided to the classifier. The image patch data for each image patch may indicate whether or not each tube slot in the tray contains a tube. From the image patch data, classifiers may be determined, using the processor, which correspond to each image patch. Methods of classifying are also described in U.S. Application No. 62/010,370 to Wu et al.

At step 312, a trained classifier may be selected for each image patch, based on the middle patch group 502, the corner patch group 504 and the center patch 506. At step 314, the processor may automatically determine whether each tube slot in the tray contains a tube using the selected trained classifier for each image patch based on the three groups 502, 504 and 506.

In some embodiments, steps 316 to 324 to determine a tube type may be performed without first using steps 306 to 314 to determine whether each tube slot in the tray contains a tube. For example, embodiments may include other methods for determining whether each tube slot in the tray contains a tube. In some embodiments, steps 316 to steps 324 may be performed under the assumption that each tube slot in the tray contains a tube. The method for determining or predicting a tube type is now described.

At step 316, the tube top patch may be extracted. That is, a plurality of image patches may be extracted over time from each image captured by cameras 242 and 244. Each image patch may be substantially centered on a top of one of the tubes 130, shown in the images at FIG. 4A and FIG. 4B. In some embodiments, the tray slot patch may be extracted, as described in U.S. Pat. No. 10,290,090 entitled "Image-based Tube Slot Circle Detection for a Vision System."

Figure 6:
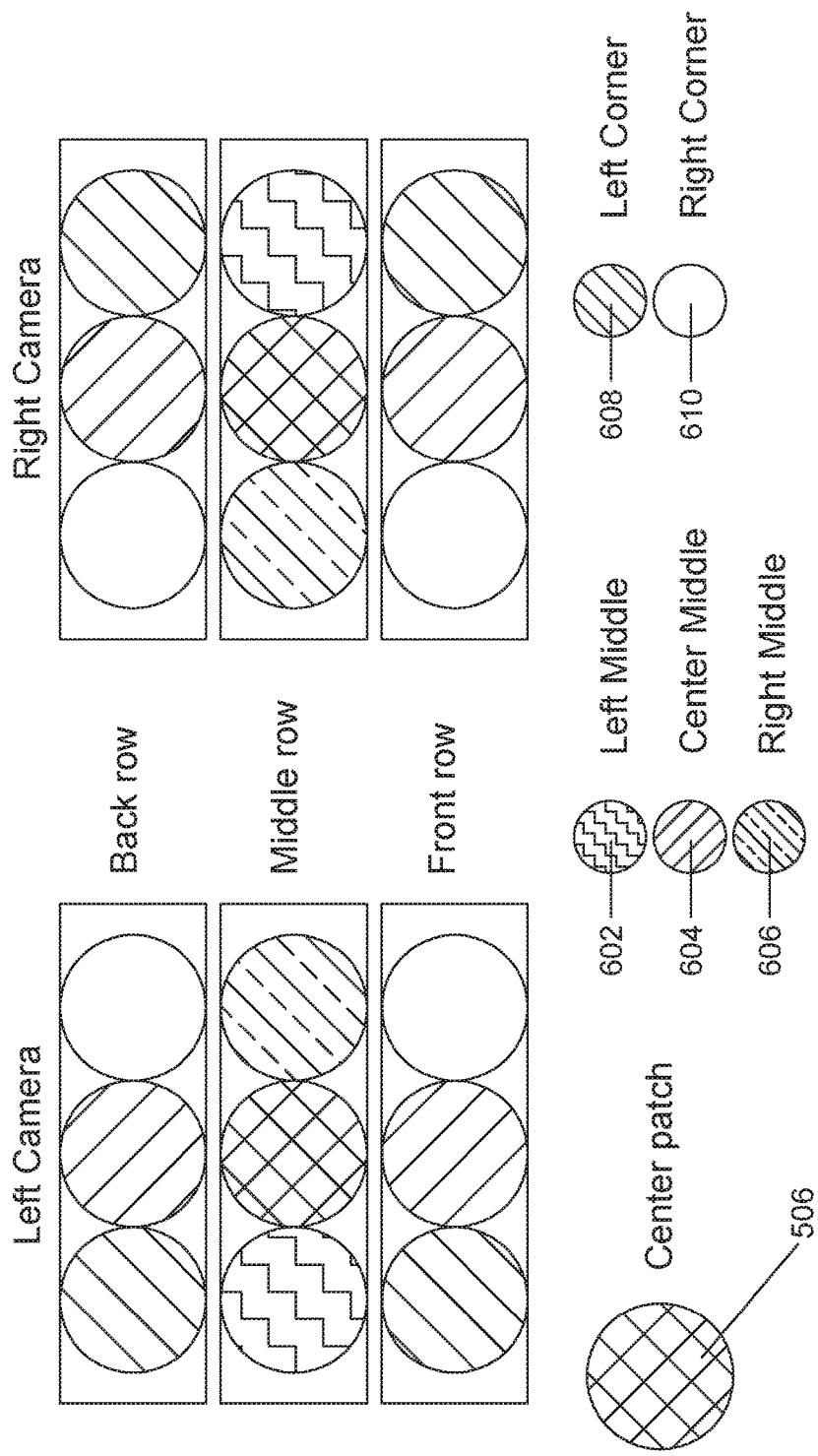
FIG. 6 is a diagram illustrating a plurality of image patches grouped into six image patch groups, according to an embodiment.

At step 318, a second location group may be assigned to each image patch. FIG. 6 is a diagram illustrating a plurality of image patches grouped into six image patch groups, according to an embodiment. As shown in FIG. 6, the second location group includes the center of the image group 506, a left corner of the image group 608, a right corner of the image group 610, a left middle of the image group 602; a center middle of the image group 604 and a right middle of the image group 606. The center of the image 506, the left middle of the image group 602 and the right middle of the image group 606 each correspond to one tube top location. The center middle of the image group 604, the left corner of the image group 608 and the right corner of the image group 610 each corresponds to two tube slot locations. The grouping applies to both the left camera 242 and the right camera 244.

Figure 7A:
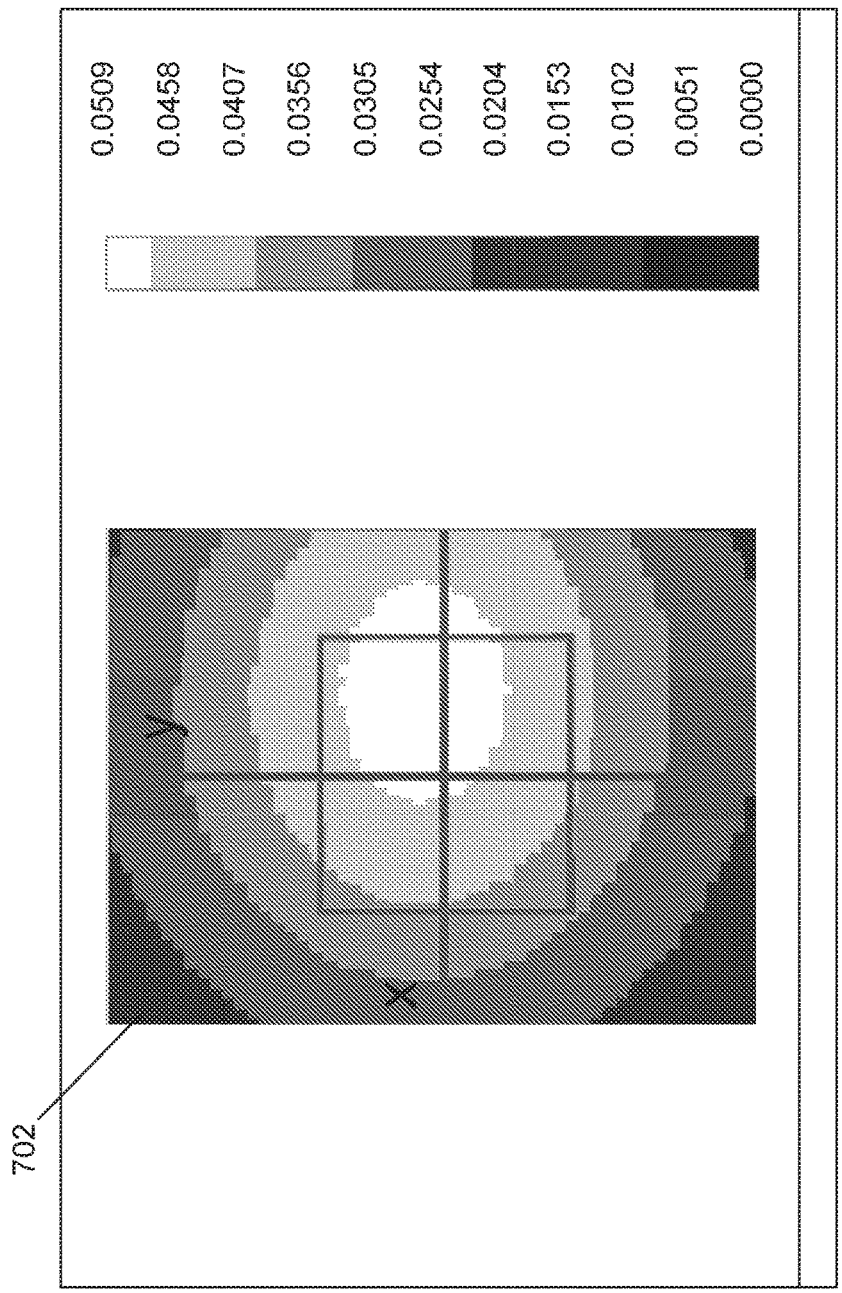
FIG. 7A is an image illustrating the light distribution of the left camera along with accompanying image data, for use with embodiments described herein.
Figure 7B:
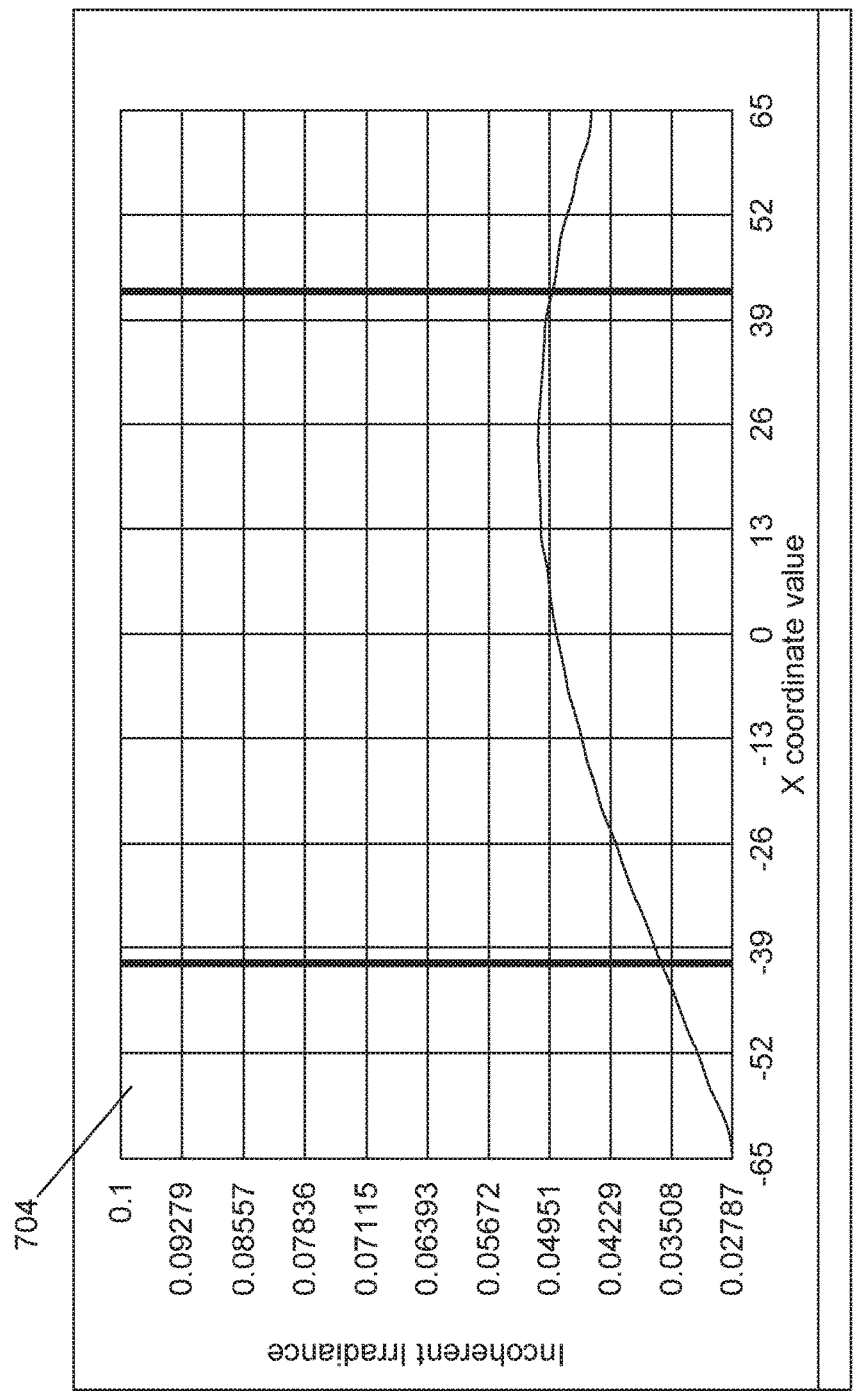
FIG. 7B is a diagram illustrating the light distribution along the X-axis of the image shown in FIG. 7A.
Figure 7C:
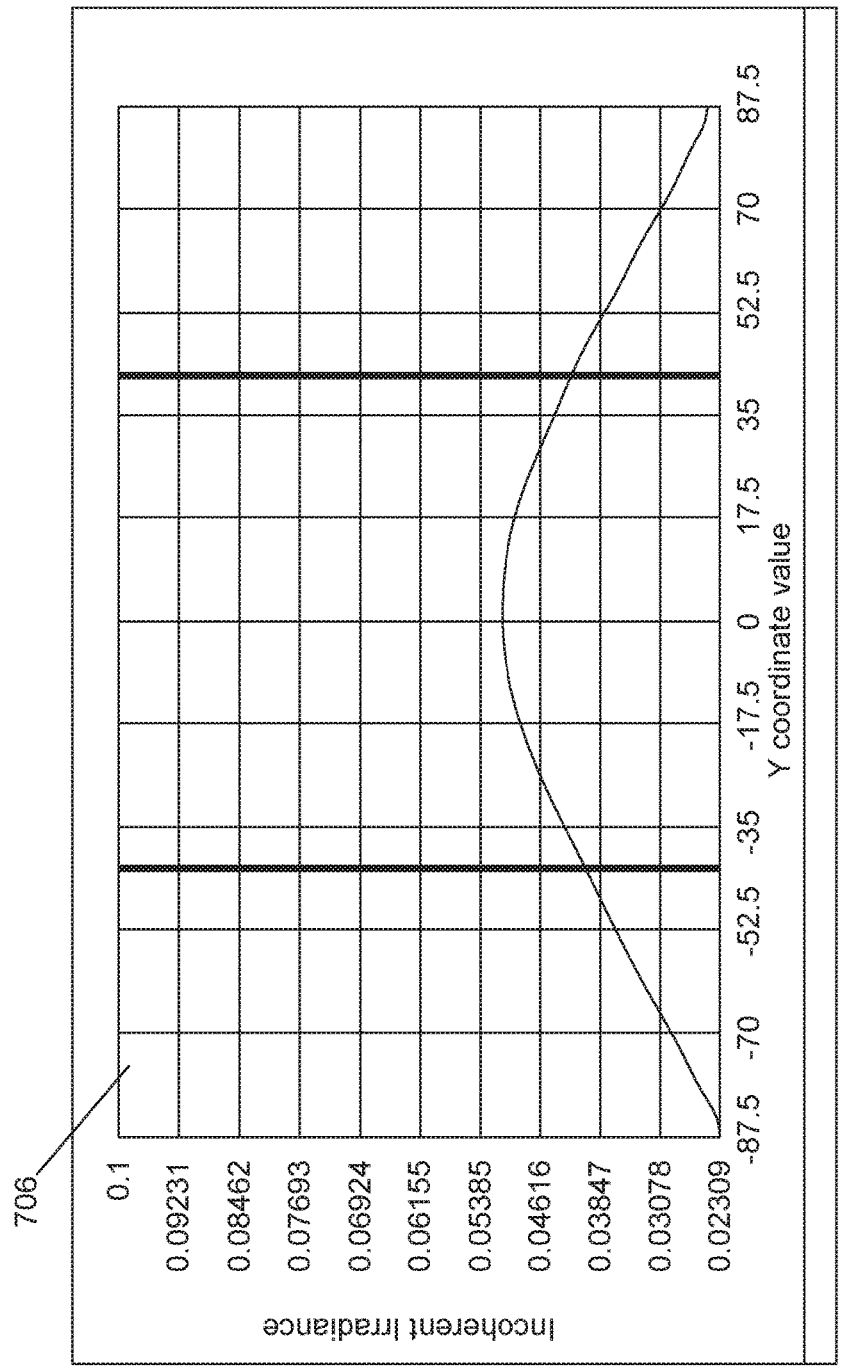
FIG. 7C is a diagram illustrating the light distribution along the Y-axis of the image shown in FIG. 7A.

The second location group is based on light distribution, such as for example the light emitted by LEDs 170 on LED board 150 shown in FIG. 2. FIG. 7A is an image 702 illustrating the light distribution of the left camera 242 along with accompanying image data, for use with embodiments described herein. FIG. 7B is a diagram 704 illustrating the light distribution along the X-axis of the image 702 shown in FIG. 7A. FIG. 7C is a diagram 706 illustrating the light distribution along the Y-axis of the image 702 shown in FIG. 7A. As shown in FIG. 7C, the light distribution of the left camera 242 is symmetric along the Y-axis. As shown in FIG. 7B, however, the light distribution of the left camera 242 is asymmetric along the X-axis.

Because the light distribution of the left camera 242 is symmetric to the light distribution of the right camera 244, the grouping of the right camera 244 is horizontally symmetric to that of the left camera 242. Accordingly, the six groups shown in FIG. 6 may be assigned to each image patch extracted from images received from the first camera 242 horizontally symmetric to each image patch extracted from images received from the second camera 244. By assigning the six groups shown in FIG. 6 to each image patch, consistency of the lighting across different patches may be achieved.

Tubes which appear at each location (patch) may be varied and that variation may be learned by the classifiers. Because the grouping of the right camera 244 is horizontally symmetric to that of the left camera 242, the same trained classifier may be selected for each image patch extracted from images received from the first camera 242 that is horizontally symmetric to each image patch extracted from images received from the second camera 244. For example, the top left patch of the left camera image patches and the top right patch of the right camera image patches are horizontally symmetrical and are part of the same group, the left corner group 608. Accordingly, these two patches may be assigned the same classifier.

Further, for the groups which have multiple patches, such as the center middle of the image group 604, the left corner of the image group 608 and the right corner of the image group 610, a row of the image patches (e.g., back row of the left camera image patches) may be used as a reference location, and other locations may be aligned, via a processor, to the corresponding reference position. The alignment can be applied as a vertical or horizontal flip, or a rotation.

Prior to selecting a trained classifier for each image patch based on the second location group at step 322 during online operation, image patch classifiers corresponding to each image patch are trained offline at step 320. An exemplary method for training image patch classifiers may be performed as described above with reference to step 310. Methods of classifying are also described in U.S. Application No. 62/010,370 to Wu et al.

At step 322, a trained classifier may be selected for each image patch, based on the six location groups shown in FIG. 6. At step 324, the processor may automatically determine at least one property of each of the tubes contained in the one or more tube slots. For example, determining at least one property of each of the tubes may include automatically determining, from the plurality image patches, whether each of the tubes contained in the one or more tube slots has a cap based on the corresponding trained classifier. Determining at least one property of each of the tubes may include automatically determining, from the plurality image patches, whether each tube contained in the one or more tube slots has a tube-top sample cup or is a plain tube based on the corresponding trained classifier.

Figure 8:
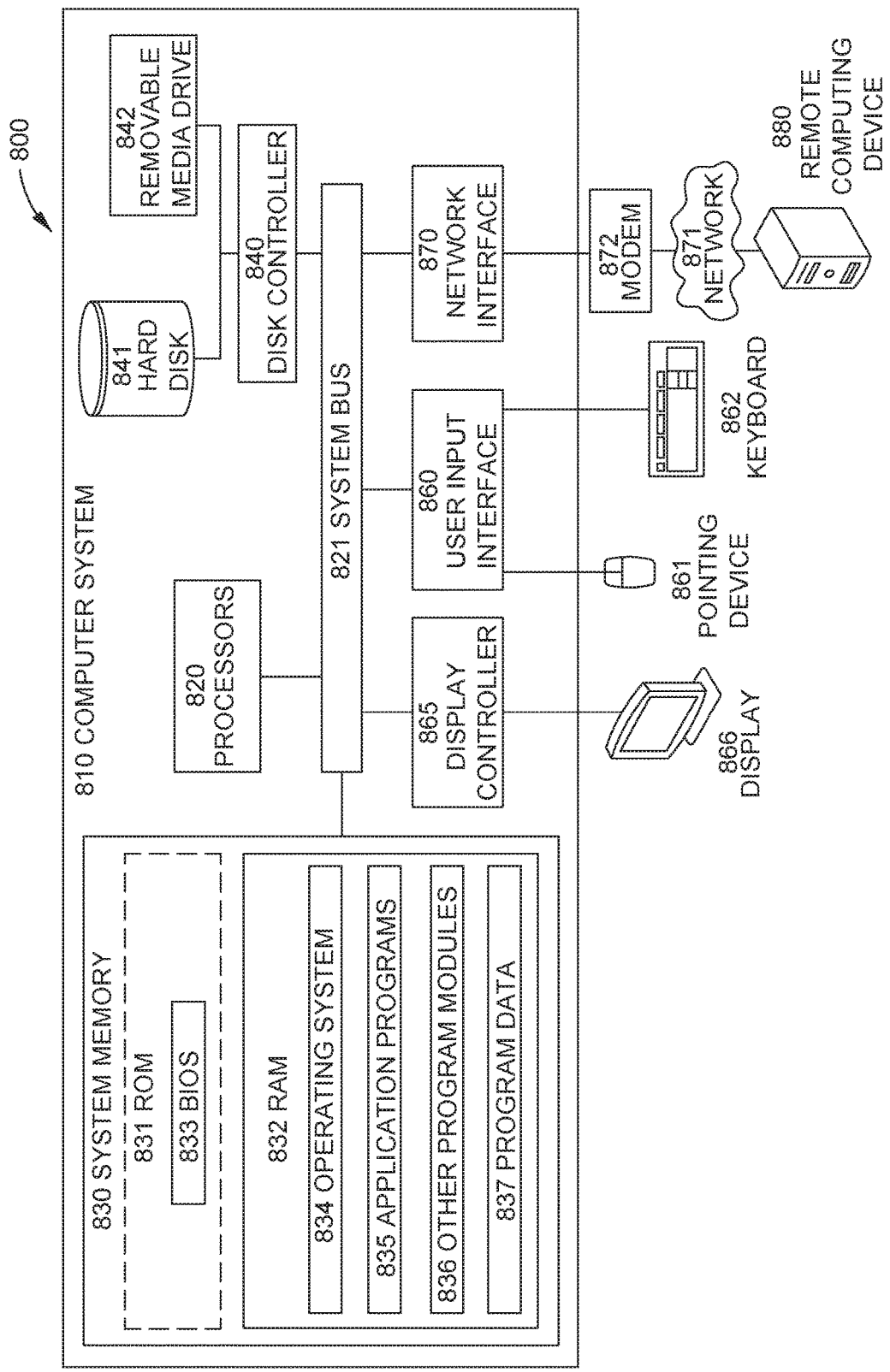
FIG. 8 illustrates an example of a computing environment within which embodiments of the invention may be implemented.

FIG. 8 illustrates an example of a computing environment 800 within which embodiments of the invention may be implemented. Computing environment 800 may be implemented as part of any component described herein. Computing environment 800 may include computer system 810, which is one example of a computing system upon which embodiments of the invention may be implemented. As shown in FIG. 8, the computer system 810 may include a communication mechanism such as a bus 821 or other communication mechanism for communicating information within the computer system 810. The system 810 further includes one or more processors 820 coupled with the bus 821 for processing the information. The processors 820 may include one or more CPUs, GPUs, or any other processor known in the art.

The computer system 810 also includes a system memory 830 coupled to the bus 821 for storing information and instructions to be executed by processors 820. The system memory 830 may include computer readable storage media in the form of volatile and/or nonvolatile memory, such as read only memory (ROM) 831 and/or random access memory (RAM) 832. The system memory RAM 832 may include other dynamic storage device(s) (e.g., dynamic RAM, static RAM, and synchronous DRAM). The system memory ROM 831 may include other static storage device(s) (e.g., programmable ROM, erasable PROM, and electrically erasable PROM). In addition, the system memory 830 may be used for storing temporary variables or other intermediate information during the execution of instructions by the processors 820. A basic input/output system 833 (BIOS) containing the basic routines that help to transfer information between elements within computer system 810, such as during start-up, may be stored in ROM 831. RAM 832 may contain data and/or program modules that are immediately accessible to and/or presently being operated on by the processors 820. System memory 830 may additionally include, for example, operating system 834, application programs 835, other program modules 836 and program data 837.

The computer system 810 also includes a disk controller 840 coupled to the bus 821 to control one or more storage devices for storing information and instructions, such as a magnetic hard disk 841 and a removable media drive 842 (e.g., floppy disk drive, compact disc drive, tape drive, and/or solid state drive). The storage devices may be added to the computer system 810 using an appropriate device interface (e.g., a small computer system interface (SCSI), integrated device electronics (IDE), Universal Serial Bus (USB), or FireWire).

The computer system 810 may also include a display controller 865 coupled to the bus 821 to control a display or monitor 866, such as a cathode ray tube (CRT) or liquid crystal display (LCD), for displaying information to a computer user. The computer system 810 includes a user input interface 860 and one or more input devices, such as a keyboard 862 and a pointing device 861, for interacting with a computer user and providing information to the processor 820. The pointing device 861, for example, may be a mouse, a trackball, or a pointing stick for communicating direction information and command selections to the processor 820 and for controlling cursor movement on the display 866. The display 866 may provide a touch screen interface which allows input to supplement or replace the communication of direction information and command selections by the pointing device 861.

The computer system 810 may perform a portion or all of the processing steps of embodiments of the invention in response to the processors 820 executing one or more sequences of one or more instructions contained in a memory, such as the system memory 830. Such instructions may be read into the system memory 830 from another computer readable medium, such as a hard disk 841 or a removable media drive 842. The hard disk 841 may contain one or more data stores and data files used by embodiments of the present invention. Data store contents and data files may be encrypted to improve security. The processors 820 may also be employed in a multi-processing arrangement to execute the one or more sequences of instructions contained in system memory 830. In alternative embodiments, hard-wired circuitry may be used in place of or in combination with software instructions. Thus, embodiments are not limited to any specific combination of hardware circuitry and software.

As stated above, the computer system 810 may include at least one computer readable medium or memory for holding instructions programmed according to embodiments of the invention and for containing data structures, tables, records, or other data described herein. The term "computer readable medium" as used herein refers to any non-transitory, tangible medium that participates in providing instructions to the processor 820 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 841 or removable media drive 842. Non-limiting examples of volatile media include dynamic memory, such as system memory 830. Non-limiting examples of transmission media include coaxial cables, copper wire, and fiber optics, including the wires that make up the bus 821. Transmission media may also take the form of acoustic or light waves, such as those generated during radio wave and infrared data communications.

The computing environment 800 may further include the computer system 810 operating in a networked environment using logical connections to one or more remote computers, such as remote computer 880. Remote computer 880 may be a personal computer (laptop or desktop), a mobile device, a server, a router, a network PC, a peer device or other common network node, and typically includes many or all of the elements described above relative to computer 810. When used in a networking environment, computer 810 may include modem 872 for establishing communications over a network 871, such as the Internet. Modem 872 may be connected to system bus 821 via network interface 870, or via another appropriate mechanism.

Network 871 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 810 and other computers (e.g., remote computing system 880). The network 871 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 871.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. Computer program instructions may be loaded onto a computer, including without limitation, a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display elements or portions thereof. A user interface (UI) comprises one or more display elements enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display elements, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the elements for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display elements in response to signals received from the input devices. In this way, the user interacts with the display elements using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

A workflow processor, as used herein, processes data to determine tasks to add to, or remove from, a task list or modifies tasks incorporated on, or for incorporation on, a task list, as for example specified in a program(s). A task list is a list of tasks for performance by a worker, user of a device, or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition. The workflow engine includes a process definition function that allows users to define a process that is to be followed and may include an event monitor. A processor in the workflow engine tracks which processes are running, for which patients, physicians, and what step needs to be executed next, according to a process definition and may include a procedure for notifying physicians of a task to be performed.

The system and processes of the figures presented herein are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Further, the processes and applications may, in alternative embodiments, be located on one or more (e.g., distributed) processing devices on a network linking the units of FIG. 8. Any of the functions and steps provided in the Figures may be implemented in hardware, software or a combination of both. No claim element herein is to be construed under the provisions of 35 U.S.C. 112, sixth paragraph, unless the element is expressly recited using the phrase "means for."

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. A method for detecting properties of sample tubes, comprising steps of:
   receiving a series of images of a tray acquired by one or more cameras, the tray having a plurality of tube slots;
   extracting, using a processor, a plurality of image patches from each image, wherein each of the plurality of image patches are substantially centered on one of a tube slot and a tube top;
   assigning, to each image patch, a first location group that defines whether the image patch is from one of: a center of the image, a corner of the image, and a middle edge of the image;
   selecting, for each image patch, based on the first location group, a trained classifier to use in processing the image patch;
   automatically determining, using the processor, from the plurality image patches, whether each tube slot in the tray contains a tube using the trained classifier for each image patch.

2. The method of claim 1, wherein the tray is configured to fit within a portion of a drawer movable between an open position and a closed position and the series of images of the tray are acquired via the one or more cameras as the drawer is moved between the open and the closed position.

3. The method of claim 1, further comprising:
   assigning, to each image patch, a second location group that defines whether the image patch is from one of: the center of the image, a left corner of the image, a right corner of the image, a left middle of the image; a center middle of the image and a right middle of the image; and selecting, for each image patch, based on the second location group, the trained classifier to use in processing the image patch, wherein, when it is determined that one or more of the tube slots contains a tube, the method further comprises automatically determining, using the processor, from the plurality image patches, at least one property of each of the tubes contained in the one or more tube slots.

4. The method of claim 3, wherein determining at least one property of each of the tubes further comprises automatically determining, using the processor, from the plurality image patches, whether each of the tubes contained in the one or more tube slots has a cap based on the corresponding trained classifier.

5. The method of claim 3, wherein determining at least one property of each of the tubes further comprises automatically determining, using the processor, from the plurality image patches, whether each tube contained in the one or more tube slots has a tube-top sample cup or is a plain tube based on the corresponding trained classifier.

6. The method of claim 3, wherein receiving the series of images further comprises receiving the series of images from a first camera and a second camera adjacent to the first camera, extracting the plurality of image patches further comprises extracting image patches from each image received from the first camera and extracting image patches from each image received from the second camera, assigning the second location group further comprises assigning the second location group to each image patch extracted from images received from the first camera horizontally symmetric to each image patch extracted from images received from the second camera, and selecting the trained classifier further comprises selecting the same trained classifier for each image patch extracted from images received from the first camera that is horizontally symmetric to each image patch extracted from images received from the second camera.

7. The method of claim 6, wherein the left corner of the image, the right corner of the image, and the center middle of the image each comprise a plurality of image patches, and assigning the second location group horizontally symmetrical further comprises:

using a row of image patches from of one of the first camera and the second camera as a reference location; and aligning image patches from the other of the first camera and the second camera to the reference location.

8. The method of claim 1, wherein each image comprises a matrix of three rows of tube slots and three columns of tube slots and the plurality of image patches comprise a matrix of three rows of image patches and three columns of image patches, each image patch corresponding to a location of one of the tube slots in the image.

9. A method for offline image patch classifier training, comprising steps of:

receiving a series of images of a tray from a plurality of cameras, the tray having a plurality of tube slots;

extracting a plurality of image patches from each image, wherein each of the plurality of image patches are substantially centered on one of a tube slot and a tube top;

providing, using a processor, each image patch of the plurality of images to a classifier;

collecting, using the processor, image patch data for each image patch provided to the classifier, the data indicating one of: whether each tube slot in the tray contains a tube; whether each of the tubes contained in the one or more tube slots has a cap; and whether each tube contained in the one or more tube slots has a tube-top sample cup or is a plain tube; and determining, using the processor, image patch classifiers corresponding to each image patch based on the image patch data.

10. The method of claim 9, wherein extracting the plurality of image patches from each image further comprising extracting, over time, multiple image patches substantially centered on one of the same tube slot and the same tube top.

11. The method of claim 9, wherein the classifier is a random forest classifier, a support vector machine classifier, or a probabilistic boosting tree classifier.

12. A vision system for use in an in vitro diagnostics environments comprising:

a tray comprising a plurality of slots arranged in a matrix of rows and columns, each tube slot configured to receive a sample tube;

a surface configured to receive the tray;

an image capture system having a first camera configured to capture a series of images of the tray; and a processor configured to:

receive the series of images of the tray captured by the first camera;

extract a plurality of image patches from each image of the series of images, wherein each of the plurality of image patches are substantially centered on one of the plurality of tube slots or a tube top;

assign, to each image patch, a first location group that defines whether the image patch is from one of: the center of the image, a corner of the image, and a middle edge of the image;

select, for each image patch, based on the first location group, a trained classifier to use in processing the image patch; and automatically determine, from the plurality of image patches, whether each tube slot in the tray contains a corresponding sample tube using the trained classifier for each image patch.

13. The system of claim 12, wherein the image capture system further comprises a second camera adjacent to the first camera and configured to capture images of the tray proximate to the images captured by the first camera.

14. The system of claim 12, wherein the surface comprises a portion of a drawer movable between an open and a closed position and the image of the tray is captured via the first camera and the second camera as the drawer is moved between the open position and the closed position.

15. The system of claim 13, wherein the processor is further configured to:

extract image patches from each image received from the first camera and extract image patches from each image received from the second camera;

assign the second location group to each image patch extracted from images received from the first camera horizontally symmetric to each image patch extracted from images received from the second camera; and select the same trained classifier for each image patch extracted from images received from the first camera that is horizontally symmetric to each image patch extracted from images received from the second camera.

16. The system of claim 13, wherein the left corner of the image, the right corner of the image, and the center middle of the image to each comprise a plurality of image patches, and the processor is further configured to assign the second location group to each image patch extracted from images received from the first camera horizontally symmetric to each image patch extracted from images received from the second camera by:

using a row of image patches from of one of the first camera and the second camera as a reference location; and aligning image patches from the other of the first camera and the second camera to the reference location.

17. The system of claim 13, wherein the image capture system further comprises a light emitting diode (LED) board comprising:

a first hole configured to facilitate the capturing of the series of images of the tray from the first camera;

a second hole configured to facilitate the capturing of the series of images of the tray from the second camera; and a plurality of LEDs arranged in a circular manner around each of the first hole and the second hole and configured to provide light on the tray.

18. The system of claim 12, wherein the processor is further configured to:

assign, to each image patch, a second location group that defines whether the image patch is from one of: the center of the image, a left corner of the image, a right corner of the image, a left middle of the image; a center middle of the image and a right middle of the image;

select, for each image patch, based on the second location group, the trained classifier to use in processing the image patch, and when it is determined that one or more of the tube slots contains a tube, the processor is further configured to automatically determine from the plurality image patches, at least one property of each of the tubes contained in the one or more tube slots.

19. The system of claim 18, wherein the processor is further configured to:

automatically determine, from the plurality image patches, whether each of the tubes contained in the one or more tube slots has a cap based on the corresponding trained classifier.

20. The system of claim 18, wherein the processor is further configured to: automatically determine, from the plurality image patches, whether each tube contained in the one or more tube slots has a tube-top sample cup or is a plain tube based on the corresponding trained classifier.

21. The system of claim 12, wherein each image comprises a matrix of three rows of tube slots and three columns of tube slots and the plurality of image patches comprise a matrix of three rows of image patches and three columns of image patches, each image patch corresponding to a location of one of the tube slots in the image.

* * * * *